ated States

McKinnis 3,938,889

Feb. 17, 1976

[54] METHOD AND APPARATUS FOR MEASURING LINEAR THERMAL EXPANSION OF POLYMERIC MATERIAL

[75] Inventor: James A. McKinnis, Rice County, Kans.

[73] Assignee: The United States of America as represented by the Secretary of the Air Force, Washington, D.C.

[22] Filed: June 4, 1974

[21] Appl. No.: 476,178

[52] U.S. Cl. .................................. 356/109; 350/3.5
[51] Int. Cl.² ........................................... G01B 9/02
[58] Field of Search .......... 356/106 R, 108, 109, 32

[56] References Cited
UNITED STATES PATENTS

| | | | |
|---|---|---|---|
| 3,424,532 | 1/1969 | Briggs et al. | 356/108 |
| 3,690,159 | 9/1972 | Kersch et al. | 356/109 |

Primary Examiner—Alfred E. Smith
Assistant Examiner—Conrad J. Clark
Attorney, Agent, or Firm—Joseph E. Rusz; Richard J. Killoren

[57] ABSTRACT

A method and apparatus for measuring the linear thermal expansion of a polymeric material wherein a sample with a wedge surface is mounted on a graphite block within a temperature controlled chamber. The incident and reflected beam of a laser lie in a plane perpendicular to the plane of the base of the sample and make equal angles with a line perpendicular to the plane of the base of the sample. A holographic plate is exposed by the object beam from the sample and a reference beam. The temperature is gradually increased from 0.9° to 4° F. between a first exposure and a second exposure. A thermocouple and indicator are used to indicate the temperature of the sample at the time of each exposure of the holographic plate. The holographic plate is then developed and replaced in the plate holder for reconstruction of the images and the fringe pattern, which indicates the expansion of the sample.

3 Claims, 8 Drawing Figures

METHOD AND APPARATUS FOR MEASURING LINEAR THERMAL EXPANSION OF POLYMERIC MATERIAL

RIGHTS OF THE GOVERNMENT

The invention described herein may be manufactured and used by or for the Government of the United States for all governmental purposes without the payment of any royalty.

BACKGROUND OF THE INVENTION

In the prior art, the most common means of measuring thermal expansion in polymeric materials are to either measure fluid or gas displacement in a closed system as the material expands or to measure the linear displacement of a mechanical rod that is placed against the material. A system is needed to more accurately measure the thermal expansion of polymeric materials.

BRIEF SUMMARY OF THE INVENTION

According to this invention, the technique of holographic interferometry is used in determining the thermal coefficient of expansion of a polymeric material. A wedge shaped sample is positioned on a graphite block with its base or back surface held to the graphite block with a silicone grease. The junction of the back surface of the sample with the graphite block is designated as the Y-Z plane and the direction perpendicular to this plane is designated the X direction.

With the tip of the wedge lying in the Y-Z plane, this edge can be used as a zero reference, since there will be no movement of this edge in the X direction due to expansion of the sample. The sample is illuminated with coherent light from a source with the reflected light from the sample being directed to a holographic plate. The light is directed toward the sample and holographic plate so that the central axis of the incident beam and the reflected light rays lies in the X direction.

IN THE DRAWING

DETAILED DESCRIPTION OF THE INVENTION

Figure 1:
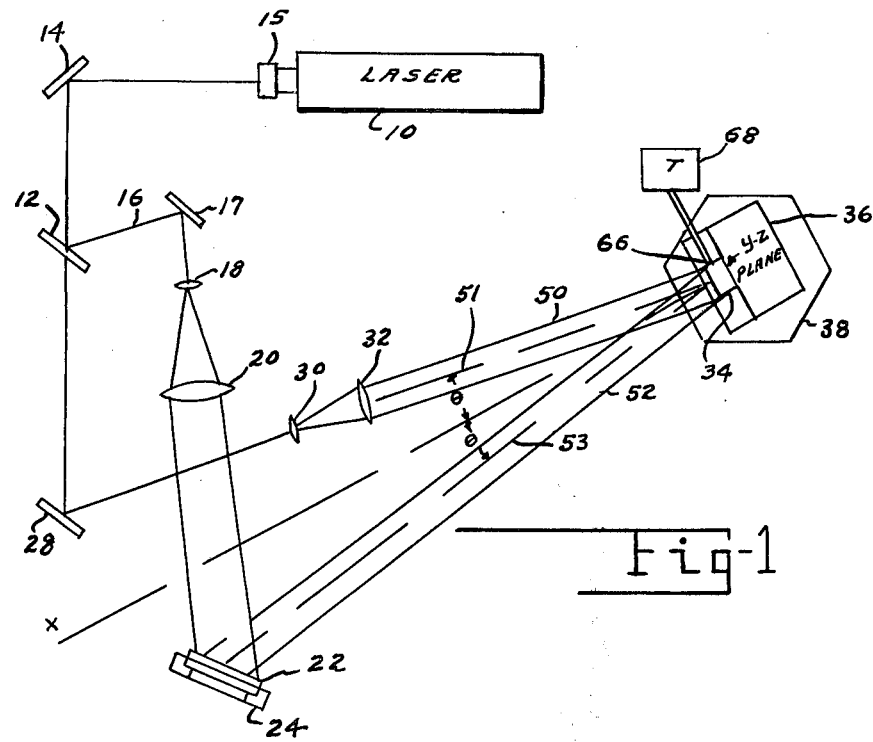
FIG. 1 is a schematic diagram showing the apparatus for measuring the linear expansion of a polymeric material.

Referring now to FIG. 1 of the drawing, which shows a conventional holographic system which is modified for use in obtaining thermal expansion information which may be used to obtain the thermal coefficient of linear expansion of the polymeric material.

The light from laser 10, which may be for example a Helium Neon laser, has its beam directed toward beam splitter 12 by means of mirror 14. A control shutter 15 controls the output of the laser. The reference beam 16 from beam splitter 12 is directed by a mirror 17 through a diverging lens 18 and collimating lens 20 to the holographic plate 22 in plate holder shown schematically at 24. The object beam from beam splitter 12 is directed by mirror 28 through diverging lens 30 and collimating lens 32 to the sample 34, with the reflected beam from the sample being directed toward holographic plate 22.

Figure 2:
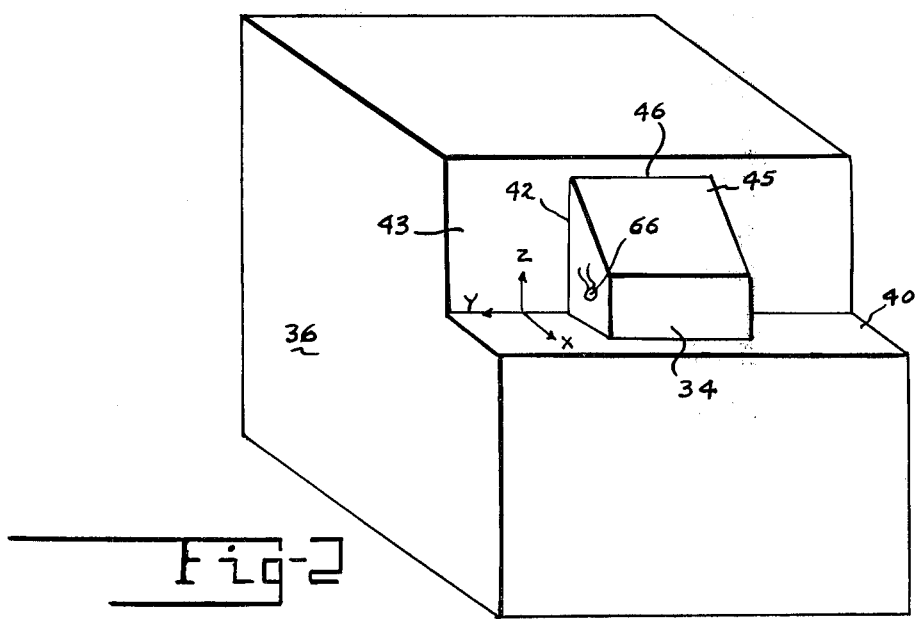
FIG. 2 is an enlarged isometric view of the sample holding member of the device of FIG. 1.

The sample is positioned on a graphite support block 36, shown in greater detail in FIG. 2, within a temperature controlled chamber 38. The sample used in one test was a polymeric solid propellant material TPH-1011 with the base surface 1 inch by 1 inch and a thickness of ½ inch. The sample 34 is positioned in a notch 40 in the graphite block 36 with the base 42 of the sample being secured to the surface 43 of the graphite block with a silicone grease. The junction of base 42 with surface 43 is designated the Y-Z plane. The sample has a wedge surface 45 with the tip 46 lying in the Y-Z plane.

The object beam is directed toward wedge surface 45 such that the incident beam 50 and the reflected beam 52 have their central beams designated 51 and 53 respectively lying in a plane perpendicular to the Y-Z plane and with the central beams 51 and 53 forming equal angles $\theta$ with a line X perpendicular to the Y-Z plane. With this arrangement, only displacements in the X directions can be resolved in the hologram.

Figure 3:
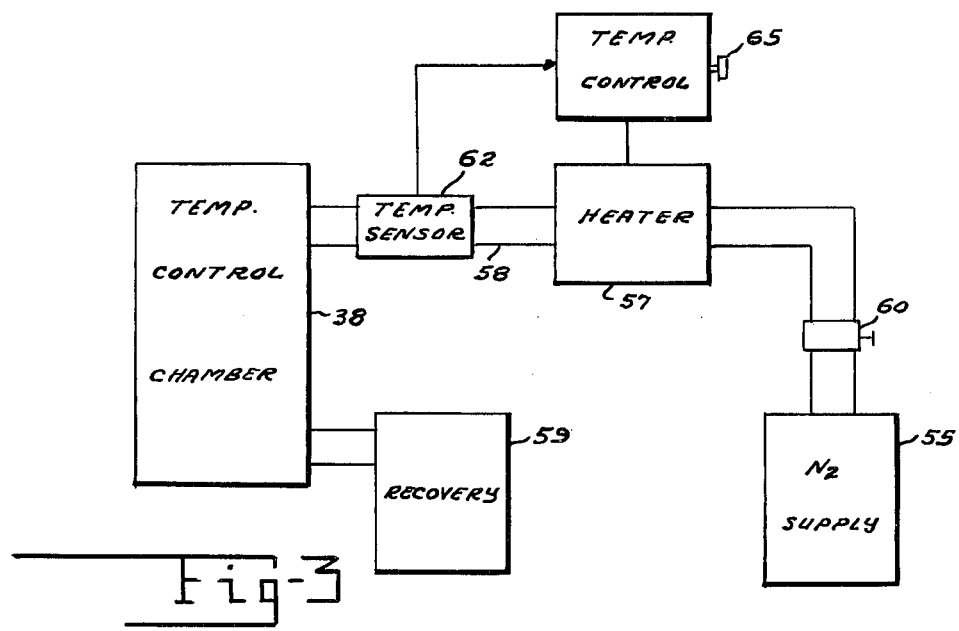
FIG. 3 is a schematic block diagram of the heating apparatus for the sample chamber of the device of FIG. 1.

The chamber 38 may be any type of insulated chamber with a window for the transmission of laser beam. The device constructed had styrofoam walls with a window of a glass such as used for photographic plates of a thickness of approximately 1 mm. Heat was supplied to the chamber as shown in FIG. 3. Nitrogen from a supply 55 passes through a heater 57 through conduit 58 to the chamber 38 and then to a recovery system 59 or to the atmosphere depending upon the gas used. The Nitrogen could be returned to the $N_2$ supply by means, not shown. The flow rate is set at a desired level by means of valve 60. The temperature of the gas to chamber 38 is maintained at the desired level by means of a temperature sensor 62 and temperature control 64. A manual control shown schematically at 65 may be used to set the desired temperature level.

In the use of the device of the invention, the sample is secured to the graphite block with a silicone grease such that the tip 46 of the wedge lies in the Y-Z plane. A thermocouple element 66 is secured to the side of the sample. The thermocouple output is applied to a temperature indicator 68. The graphite block and sample are then positioned in the temperature control chamber 38 with the sample in the path of the object ray 50. The temperature on the indicator 68 is then recorded. With the sample at a given temperature, the shutter 15 is opened to illuminate the holographic plate 22 with reference beam 16 and object beam 53 for a predetermined interval of time such as 2 to 3 seconds. The laser shutter 15 is then closed and temperature in the chamber 38 is raised in 0.5° increments each of about 10 to 15 minutes duration until the final desired temperature is reached. In samples measured, these temperatures were from 0.9° to 4°F. above room temperature. After the temperature in the chamber reaches the desired temperature, the chamber is held at that temperature for from 30 to 45 minutes to allow the sample to equiliberate.

After the equilibration time, the shutter 15 is again opened to again illuminate the holographic plate 22 for about 2 or 3 seconds with the reference beam 16 and the object beam 53. The temperature on the indicator 68 is again recorded.

Figure 5:
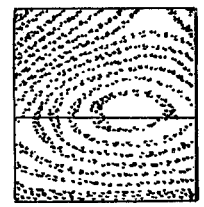
FIG. 5 is a diagram representing a reconstructed image of a nonuniformly expanded polymeric sample.

After the shutter 15 is again closed, the holographic plate is then removed from the plate holder and developed in the usual manner. After development, the holographic plate is again replaced in the plate holder 24 and illuminated with the reference beam with the object beam blocked, to reconstruct the sample image with the interference fringes as shown schematically in FIG. 4. If hot spots developed in the sample due to improper heating of the sample, a fringe pattern such as illustrated in FIG. 5 may be produced in the reconstructed image. When this happens, it indicates nonuniform heat distribution in the sample and the holographic plate is discarded.

Figure 4:
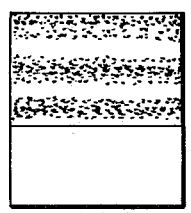
FIG. 4 is a diagram representing a reconstructed image of a uniformly expanded polymeric sample.

With a uniform fringe pattern, such as shown in FIG. 4, the number of fringes on the wedge surface 45 will provide a direct measurement of the linear expansion of the sample. This can be used to determine the thermal coefficient of linear expansion as follows.

The change in an objects length due to a thermal change can be calculated by:

$$\Delta l = (l)(\alpha)(\Delta T)$$

where
$l$ = original thickness in X direction
$\Delta l$ = change in thickness in X direction
$\alpha$ = thermal coefficient of linear expansion
$\Delta T$ = change in temperature The expansion of the graphite block is small, about one-tenth that of the sample, however this need not be considered in taking the measurements since the wedge tip indicates a line of zero expansion of the sample block.

In holographic interferometry, fringe patterns are produced if the object is displaced betweeen exposures. The displacement is related to the fringe pattern by:

$$\Delta l = \frac{\eta \lambda}{2 \cos \theta}$$

where
$\eta$ = Number of fringes on wedge surface
$\lambda$ = Wavelength of laser light
$2\theta$ = Angle between incident and reflected light rays off object surface.

With the angle between the incident beam and the X axis made equal to the angle between the reflected beam and the X axis, the angle $\theta$ will be equal to these angles.

By equating these two equations and solving for $\alpha$, we find:

$$\alpha = \frac{\eta \lambda}{(\Delta T)(l) 2 \cos \theta}$$

in one device measured
$\theta = 16°$ ($\cos \theta = 0.96$)
$l = 0.5$ inch
$\lambda = 6328A = 24.88 \times 10^{-6}$ inches
Putting these values into the equation for $\alpha$ we find:

$$\alpha = \frac{\eta}{\Delta T}(25.92 \times 10^{-6}) \text{in/in/°F}$$

Therefore, the thermal coefficient of linear expansion can be found from the number of fringes on the wedge surface and the change in temperature.

The starting temperature at which the first exposure is taken need not be room temperature, but may be any temperature desired as long as the sample is brought to that temperature slowly and allowed to equiliberate at that temperature. Also, the temperature need not be raised in definite increments but may be raised gradually by some automatic means up to the desired temperature over a long period of time, for example one hour for a 4° temperature rise. A drop of a few degrees in temperature can also be used to determine the coefficient of linear expansion.

While a fixed time holographic system has been described, real time holography could also be used. In this system, the holographic plate would be removed and developed after the first exposure at room temperature. The holographic plate would be replaced in the holder after the sample has been raised to the desired temperature level. A three dimensional image of the sample would be reconstructed by illuminating the developed hologram with the reference beam. If the object beam is allowed to illuminate the sample at the same time, interference fringes will appear on the surface of the sample. These fringes may be used to determine the thermal coefficient of linear expansion as described above.

Figure 6:
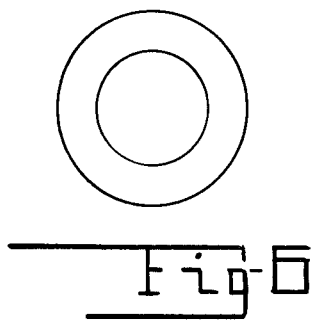
FIG. 6 is a plan view of an alternate sample shape which may be used with the device of the invention.
Figure 7:
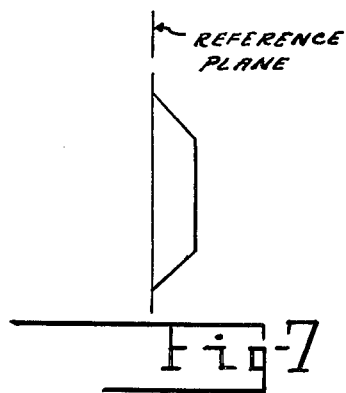
FIG. 7 is a left side view of the device of FIG. 6.
Figure 8:
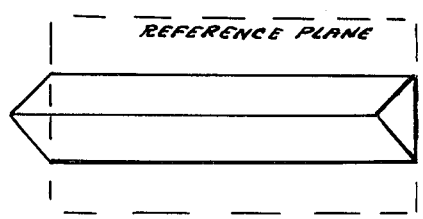
FIG. 8 shows another sample shape which may be used with the device of the invention.

The sample may have other shapes than that shown, such as a disk shaped member with a wedge shaped edge as shown in FIGS. 6 and 7 or a triangular shaped member, as shown in FIG. 8. For other applications, other shapes may be desirable as long as a line of zero expansion is provided.

There is thus provided a method and apparatus for determining the linear expansion of a polymeric material and which will give an indication of nonuniform expansion.

I claim:

1. The method of measuring the linear thermal expansion of a sample of a polymeric material for determining the coefficient of linear expansion of the material, comprising: preparing a wedge shaped sample of polymeric material having a sharp tip; positioning the wedge shaped sample on a graphite block within a temperature controlled chamber; securing the base of the wedge shaped sample to the graphite block with the tip of the wedge lying in the plane of the junction of the sample base and a surface of the graphite block; recording the temperature of the sample; directing a collimated coherent laser object beam toward said sample; positioning a holographic plate in the path of reflected light from said sample, with the central beam path of the incident beam on the sample and the central beam of the reflected beam from said sample to the holographic plate lying in a plane perpendicular to the plane of the junction of the sample base and the surface of the graphite block and being at equal angles with respect to a line perpendicular to the plane of the junction of the sample base and the surface of the graphite block; directing a collimated reference beam toward said holographic plate; blocking said object beam and said reference beam after a predetermined exposive time interval; heating the sample at small temperature increments to a predetermined temperature above the original measured temperature; allowing the sample to remain at such predetermined temperature for between 30 to 45 minutes; recording the sample temperature after expansion of the sample; exposing said holographic plate a second time to said reference beam and the reflected beam from said sample; blocking the reference beam and the object beam after a predetermined exposure time interval; removing the holographic plate; developing the holographic plate; restoring the holographic plate to its former position; illuminating the holographic plate with only the reference beam to reconstruct the sample images with the fringe pattern thereon which provide an indication of the thermal expansion of the polymeric sample.

2. The method of measuring the linear thermal expansion of a sample of a polymeric material for determining the coefficient of linear expansion of the material, comprising: preparing a wedge shaped sample of polymeric material having a sharp tip; positioning the wedge shaped sample on a graphite block within a temperature controlled chamber; securing the base of the wedge shaped sample to the graphite block with the tip of the wedge lying in the plane of the junction of the sample base and a surface of the graphite block; recording the temperature of the sample; directing a collimated coherent laser object beam toward said sample; positioning a holographic plate in the path of reflected light from said sample with the central beam path of the incident beam on the sample to the holographic plate lying in a plane perpendicular to the plane of the junction of the sample base and the surface of the graphite block; and being at equal angles with respect to a line perpendicular to the plane of the junction of the sample base and the surface of the graphite block; directing a collimated reference beam toward said holographic plate; blocking and object beam and said reference beam after a predetermined exposure time interval; removing the holographic plate; developing the holographic plate; restoring the holographic plate in its former position; heating the sample at small temperature increments to a predetermined temperature above the original measured temperature; allowing the sample to remain at said predetermined temperature for between 30 and 45 minutes; recording the sample temperature after expansion of the sample; illuminating said holographic plate with said reference beam and the sample with the object beam to reconstruct the sample image on the sample with a resulting fringe pattern thereon which provide an indication of the thermal expansion of the polymeric sample.

3. An apparatus for measuring the linear thermal expansion of a polymeric material; comprising; a temperature controlled chamber; a graphite block within said chamber; a notch on said block for holding a sample of said polymeric material; a sample of said polymeric material positioned in said notch; said sample having a wedge surface; means for securing the base of the sample to the surface of the graphite block with the tip of the wedge lying in the plane of the junction of the sample base and the surface of the graphite block; a window in said chamber for passing laser light to said sample; means for directing an object beam of collimated coherent light toward said sample; a holographic plate positioned in the path of reflected light from said sample with the central beam of the light incident on said sample and the central beam of the light reflected from said sample being in a plane perpendicular to the plane of the junction of the sample base and the surface of the graphite block and making equal angles with respect to a line perpendicular to the plane of the junction of the sample base and the surface of the graphite block; means, for directing a collimated reference beam toward said holographic plate; means for selectively blocking the light in said object beam and said reference beam; means for adjusting the temperature within said chamber and means for indicating the temperature of the sample within the chamber.

* * * * *